| United States Patent [19] | [11] Patent Number: 4,824,992 |
| Tanaka et al. | [45] Date of Patent: Apr. 25, 1989 |

[54] PROCESS FOR PRODUCING PYROMELLITIC ACID

[75] Inventors: Toru Tanaka; Tomiyoshi Furuta; Kazue Suwa, all of Kurashiki, Japan

[73] Assignee: Mitsubishi Gas Chemical Company, Inc., Tokyo, Japan

[21] Appl. No.: 104,892

[22] Filed: Oct. 6, 1987

[30] Foreign Application Priority Data

Nov. 20, 1986 [JP] Japan ................. 61-275329

[51] Int. Cl.⁴ .......................................... C07C 51/265
[52] U.S. Cl. .................................................. 562/416
[58] Field of Search ........................................ 562/416

[56] References Cited

U.S. PATENT DOCUMENTS 4,719,311 1/1988 Partenheimer ...................... 562/413

FOREIGN PATENT DOCUMENTS 83224 7/1983 European Pat. Off. ............ 562/416
2749638 5/1978 Fed. Rep. of Germany .
2463116 2/1981 France .
55-17348 2/1980 Japan ................................... 562/416

OTHER PUBLICATIONS

Chemical Abstracts, vol. 106, Feb. 9, 1987, No. 6.

*Primary Examiner*—Michael L. Shippen
*Attorney, Agent, or Firm*—Armstrong, Nikaido, Marmelstein & Kubovcik

[57] ABSTRACT

A process for producing pyromellitic acid which comprises oxidizing 2,4,5-trimethylbenzaldehyde with a gas containing molecular oxygen in the presence of a water solvent containing 0.5 to 12% by weight of bromine ion, 0.01 to 2.0% by weight of manganese ion and 0.1 to 10,000 ppm by weight of iron ion.

According to the present invention, pyromellitic acid can be obtained in a high yield and, at the same time, the amount of remaining intermediate compounds such as methyltrimellitic acid and the like can be made few, so that pyromellitic acid can be purified easily.

3 Claims, No Drawings

PROCESS FOR PRODUCING PYROMELLITIC ACID

BACKGROUND OF THE INVENTION

1. Field of the Invention

The present invention relates to a process for producing pyromellitic acid by oxidizing 2,4,5-trimethylbenzaldehyde. Pyromellitic acid is useful as a raw material of special plasticizers, polyamides, imides, and the like.

2. Description of the Prior Art

The process for producing aromatic carboxylic acids by oxidizing aromatic hydrocarbons having an alkyl group or a partially oxidized substituent is stated in U.S. Pat. Nos. 2,276,774 and 2,245,528, wherein is disclosed a process using a lower aliphatic carboxylic acid such as acetic acid as a solvent in the presence of a heavy metal and a bromine compound.

This process is disadvantageous in that it uses a lower aliphatic carboxylic acid as solvent and hence combustion of the solvent inevitably takes place and that the process must involve a step for recovering the solvent.

In view of above, Japanese Patent Publication No. 13,921/64 disclosed a process which comprises oxidizing an aromatic compound in the presence of bromine ion in an aqueous solvent, and Japanese Patent Publication No. 2,222/83 disclosed a process which comprises oxidizing 2,4-dimethylbenzaldehyde or 2,4,5-trimethylbenzaldehyde in an aqueous solvent in the presence of a catalyst consisting of a bromine compound and a metal selected from manganese and cerium.

Although the process which comprises oxidizing 2,4,5-trimethylbenzaldehyde in a water solvent is advantageous in that solvent is not lost by combustion and a recovery of solvent is unnecessary, it is disadvantageous in that the oxidation rate is low and a high yield is not readily achievable.

That is, due to the low reactivity, intermediate products such as methyltrimellitic acid and the like remain in the resulting reaction mixture which makes the purification of pyromellitic acid difficult. Further, when the oxygen concentration in waste gas is enhanced by increasing the flow rate of air or when the reaction temperature is elevated or the catalyst concentration is altered, the amount of combustion increases to increase the formation of carbon dioxide which results in a decrease in the product yield.

SUMMARY OF THE INVENTION

With the aim of overcoming the above-mentioned problems in the production of pyromellitic acid by oxidation of 2,4,5-trimethylbenzaldehyde in a water solvent, the present inventors conducted many studies to find that pyromellitic acid can be obtained in a high yield when the oxidation is carried out in a water solvent in the presence of a combined catalyst consisting of bromine ion, manganese ion and iron ion of which concentrations are in specified ranges. Based on this finding, the present invention was accomplished.

Thus, the present invention provides a process for producing pyromellitic acid which comprises oxidizing 2,4,5-trimethylbenzaldehyde with a gas containing molecular oxygen in an water solvent containing 0.5 to 12% by weight of bromine ion, 0.01 to 2.0% by weight of manganese ion and 0.1 to 10,000 ppm by weight of iron ion.

The bromine source used in the invention may be any bromine source so far as it generates bromine ion in itself or it functions as a precursor of such a bromine source. For example, hydrogen bromide, manganese bromide, iron bromide and the like can be used for this purpose. Concentration of bromine ion is 0.5 to 12% by weight and preferably 0.5 to 6% by weight based on the water solvent.

As the manganese ion source, manganese hydroxide, manganese carbonate, manganese bromide and the like can be used. Concentration of manganese ion is 0.01 to 2.0% by weight and preferably 0.05 to 1.0% by weight based on the water solvent. Preferably, molar ratio of manganese ion to bromine should be 1.0 or below.

As the iron ion source, bromide, oxide, hydroxide and the like of iron, including $Fe^{++}$ and/or $Fe^{+++}$, can be used. Concentration of iron ion is 0.1 to 10,000 ppm by weight, preferably 1.0 to 1,000 ppm by weight and more preferably 3.0 to 200 ppm by weight based on the solvent. If the iron ion concentration is too low, the product yield is low. If iron ion concentration is too high, an insoluble material is formed to cause troubles in the subsequent steps.

In the present invention, water is used as a solvent. The use of water solvent is advantageous in that the solvent is not lost by combustion. Though the amount of solvent is not critical, it is preferably used in at least equal amount to the starting 2,4,5-trimethylbenzaldehyde.

The reaction temperature is 180° C. to 280° C., and preferably 200° C. to 250° C. If it is lower than 180° C., the reaction cannot progress substantially. If it is too high, combustion of 2,4,5-trimethylbenzaldehyde takes place to a marked extent.

The pressure may be any pressure so far as it is a pressure capable of maintaining the reaction mixture in a liquid phase. Usually, the pressure is in the range of 10 to 80 kg/cm²G.

As the molecular oxygen-containing gas, oxygen gas, a mixture of oxygen gas and an inert gas such as nitrogen, and air are all usable. Among these gases, air is most economical. If the amount of air is too large and the oxygen concentration in waste gas is increased, combustion of the feed stock takes place too much. If it is too small, tarry substance is formed to lower the yield of product. Oxygen concentration in the waste gas is 1.5 to 8% by volume, and preferably 2 to 6% by volume.

The reaction may be carried out by any of a batch process, a semi-continuous process and a continuous process.

After the reaction, the product is recovered from reaction system in the following manner. Thus, firstly, the pressure of reaction system is decreased to atmospheric pressure and the oxygen dissolved in the reaction mixture is released. Next, the product is crystallized under a reduced pressure. After crystallization of the product, the product is washed with rinsing water. Finally, it is dried with hot air to obtain the product.

FUNCTION AND EFFECT OF THE INVENTION

As compared with the prior arts (Japanese Patent Publication No. 2,222/83) which comprises oxidizing 2,4,5-trimethylbenzaldehyde in a water solvent containing bromine ion and metallic ion selected from manganese ion and cerium ion, the process of the present invention using a catalyst additionally containing iron ion gives an increased yield of pyromellitic acid with a smaller formation of carbon dioxide even if the oxygen concentration in waste gas is enhanced. Based on this fact, it is presumable that iron ion has an effect of preventing the combustion of 2,4,5-trimethylbenzaldehyde.

According to the invention, the yield of pyromellitic acid is improved and, at the same time, the amount of remaining intermediate products such as methyltrimellitic acid and the like can be decreased, so that pyromellitic acid can be purified easily.

Owing to these effects, the present invention has an important industrial significance.

DESCRIPTION OF THE PREFERRED EMBODIMENTS

Next, the invention will be illustrated more concretely with reference to examples in no limitative way.

EXAMPLES 1 TO 6

An aqueous solution containing bromine ion, manganese ion and iron ion of which quantities were as shown in Table 1 was charged into a 2 liter autoclave made of zirconium equipped with a reflux condenser, a stirrer and a heater.

As the manganese ion source, manganese bromide tetrahydrate ($MnBr_2 \cdot 4H_2$) was used. As the iron ion source, ferric bromide was used. The bromine ion source was prepared by adding hydrobromic acid to these bromides.

After elevating the inner pressure with nitrogen, the temperature was elevated and adjusted to 240° C. Then, air was introduced at a rate of 330 liters/hour and the reaction pressure was adjusted to 50 kg/cm$^2$G. Then, 2,4,5-trimethylbenzaldehyde was fed at a rate of 80 g/hour over a period of 2 hours, after which air was passed for 20 minutes and the reaction mixture was cooled. After completion of the reaction, the reaction mixture was taken out and analyzed by means of gas chromatography to determine the yield of pyromellitic acid. The yield of pyromellitic acid and the concentration of carbon dioxide in waste gas at varied ion concentrations were as shown in Table 1.

COMPARATIVE EXAMPLES 1 TO 4

The reaction was carried out in the same manner as in Examples 1 to 6, except that the concentrations of bromine ion, manganese ion and iron ion were out of the ranges specified in the present invention. The results obtained are shown in Table 1 as "Comparative Examples".

In all these comparative examples, the yield of pyromellitic acid was lower than that in Examples 1 to 6, demonstrating that each ion has an optimum concentration range.

TABLE 1

|  | Bromine ion concentration (% by wt.) | Manganese ion concentration (% by wt.) | Iron ion concentration (ppm by wt.) | Yield of pyromellitic acid (% by mole) | $CO_2$ concentration in waste gas (% by vol.) |
|---|---|---|---|---|---|
| Example |  |  |  |  |  |
| 1 | 3.0 | 0.5 | 30 | 88.0 | 2.9 |
| 2 | 3.0 | 0.5 | 100 | 89.0 | 2.5 |
| 3 | 3.0 | 0.5 | 1000 | 89.0 | 1.9 |
| 4 | 3.0 | 0.1 | 30 | 84.0 | 3.5 |
| 5 | 3.0 | 0.7 | 30 | 85.0 | 3.3 |
| 6 | 3.0 | 0.9 | 30 | 85.0 | 3.4 |
| Comparative Example |  |  |  |  |  |
| 1 | 0.1 | 0.5 | 30 | 35.0 | 6.0 |
| 2 | 0.2 | 0.5 | 0.01 | 62.0 | 7.0 |
| 3 | 15.0 | 0.5 | 20 | 58.0 | 6.0 |
| 4 | 0.3 | 0.001 | 25 | 53.0 | 6.5 |

What is claimed is:

1. A process for producing pyromellitic acid which comprises oxidizing 2,4,5-trimethylbenzaldehyde with a gas containing molecular oxygen at a reaction temperature in the range of 180° C. in the presence of a water solvent containing 0.5 to 12% by weight of bromine ion, 0.01 to 2.0% by weight of manganese ion and 0.1 to 10,000 weight of iron ion.

2. A process for producing pyromellitic acid according to claim 1, wherein molar ratio of manganese ion to bromine ion is 1.0 or below.

3. A process for producing pyromellitic acid according to claim 1, wherein the oxygen concentration in the waste gas after the oxidation is in the range of 1.5 to 8% by volume.

* * * * *